United States Patent
Hakii et al.

(10) Patent No.: US 7,927,804 B2
(45) Date of Patent: Apr. 19, 2011

(54) METHOD OF FORMING SIGNAL PROBE-POLYMER

(75) Inventors: Chikako Hakii, Yokohama (JP); Mitsugu Usui, Yokohama (JP)

(73) Assignee: Eisai & Managment Co., Ltd., Tokyo (JP)

( * ) Notice: Subject to any disclaimer, the term of this patent is extended or adjusted under 35 U.S.C. 154(b) by 156 days.

(21) Appl. No.: 12/225,062

(22) PCT Filed: Mar. 14, 2007

(86) PCT No.: PCT/JP2007/055036
§ 371 (c)(1),
(2), (4) Date: Sep. 12, 2008

(87) PCT Pub. No.: WO2007/108378
PCT Pub. Date: Sep. 27, 2007

(65) Prior Publication Data
US 2010/0248222 A1 Sep. 30, 2010

(30) Foreign Application Priority Data
Mar. 15, 2006 (JP) .................. 2006-071617

(51) Int. Cl.
*C12Q 1/68* (2006.01)
*C07H 21/02* (2006.01)
*C07H 21/00* (2006.01)
*C07H 19/04* (2006.01)
*C12Q 1/70* (2006.01)
*G01N 33/53* (2006.01)

(52) U.S. Cl. .................. 435/6; 435/5; 435/7.1; 435/7.2; 536/24.3; 536/24.33; 536/25.3; 536/26.6

(58) Field of Classification Search .................. 435/5, 6, 435/7.1, 7.2; 536/23.1, 24.3, 24.33, 25.3, 536/26.6
See application file for complete search history.

(56) References Cited

U.S. PATENT DOCUMENTS
2001/0019835 A1   9/2001   Usui
2003/0008294 A1   1/2003   Usui et al.
(Continued)

FOREIGN PATENT DOCUMENTS
EP   2000-201687   7/2000
(Continued)

OTHER PUBLICATIONS

European Office Action issued Aug. 26, 2010 in corresponding European Patent Application No. 07 73 8507.

*Primary Examiner* — Jezia Riley
(74) *Attorney, Agent, or Firm* — Wenderoth, Lind and Ponack, L.L.P.

(57) ABSTRACT

Provided are a method of forming a signal probe-polymer which makes it possible to form a polymer efficiently and quantitatively, a signal probe-polymer formed by the method, oligonucleotide probes for use in the method, and a method of detecting target analyte having high sensitivity and excellent quantitative capability. The method of forming a signal probe-polymer comprises reacting a plurality of pairs of oligonucleotide probes with each other to form a polymer, a first probe of the pair of oligonucleotide probes comprising three nucleic acid regions of X, Y, and Z regions, located in the stated order from the 5'-terminal and a second probe comprising three nucleic acid regions of X', Y', and Z' regions, located in the stated order from the 5'-terminal, wherein each region of the oligonucleotide probes has a length of from 13 to 15 bases.

17 Claims, 6 Drawing Sheets

U.S. PATENT DOCUMENTS

2006/0210983 A1  9/2006  Usui et al.

FOREIGN PATENT DOCUMENTS

| | | |
|---|---|---|
| EP | 1 188 841 | 3/2002 |
| EP | 1 002 877 | 9/2005 |
| EP | 1 595 953 | 11/2005 |
| JP | 2002-355081 | 12/2002 |
| JP | 2003-164299 | 6/2003 |
| WO | 01/75157 | 10/2001 |
| WO | 02/18642 | 3/2002 |
| WO | 02/31192 | 4/2002 |
| WO | 03/029441 | 4/2003 |
| WO | 2004/074480 | 9/2004 |
| WO | 2005/106031 | 11/2005 |

METHOD OF FORMING SIGNAL PROBE-POLYMER

This application is a U.S. national stage of International Application No. PCT/JP2007/055036 filed Mar. 14, 2007.

TECHNICAL FIELD

The present invention relates to a method of forming a signal probe-polymer which makes it possible to form a self-assembly substance (polymer) of oligonucleotide probes efficiently, and which can contribute to enhance stability and sensitivity of detection of a target analyte, a polymer formed by the method, a method of detecting the target analyte using the method, and a pair of probes used for the method.

BACKGROUND ART

The inventors of the present invention have proposed a novel isothermal nucleic acid amplification method (a method of forming a self-assembly substance of probes) which is free from enzyme (Patent Documents 1 to 4). FIGS. 1 to 3 are schematic drawings explaining a method described in Patent Document 1. For example, the method described in Patent Document 1 is a method, as illustrated in FIG. 1, which uses a pair of oligonucleotide probes 18 (Honey Comb Probe; hereinafter, referred to as HCP), each of which is constituted of three regions. The respective three regions of the first HCP 18a (an X region, a Y region, and a Z region) and the respective three regions of the second HCP 18b (an X' region, a Y' region, and a Z' region) have base sequences which are complementary to each other, and, when the both probes are reacted with each other, the base sequences of the respective regions are arranged suitably so that each region in one probe hybridizes with a specific region in the other probe (FIG. 2). When a plurality of pairs of HCPs are reacted, the above idea makes it possible to form a self-assembly substance 20 (polymer) of probes through hybridization of the pair of HCPs with each other (FIG. 3). In the present description, the method of forming a polymer through the above self-assembly reaction of these oligonucleotide probes (an oligonucleotide probe alternation link self-assembly reaction) is referred to as a PALSAR method.

The method described in Patent Document 2 relates to a method of forming a more stable polymer efficiently, in which guanine or cytosine is placed at the terminal of each region in the pair of HCPs, whereby a C—G bond is formed at the terminal of each region when the pair of HCPs are hybridized with each other. In examples of Patent Document 2, there is disclosed the HCP having 20 bases in each region and having G or C at the terminal of each region.

In addition, the inventors of the present invention have found that the use of the PALSAR method contributes to enhance the sensitivity of detecting a target gene (Patent Document 5). FIG. 4 shows an example of a signal amplification method on a microplate by using the PALSAR method. As shown in FIG. 4(a), a capture probe 14 (a probe for capturing) that can capture a target nucleic acid 12 is bonded to a reaction material such as a microplate 10; then, the target nucleic acid 12 is captured by the capture probe 14 as described in FIG. 4(b); an assist probe 16 having regions each being complementary to HCPs and the target nucleic acid is added as shown in FIG. 4(c); a plurality of pairs of HCPs 18 are further added as shown in FIG. 4(e), to thereby form a self-assembly substance 20 through an alternation link self-assembly reaction; and whereby being capable of amplifying a signal.

It should be noted that the signal probe-polymer (simply referred to as a polymer, too) in the present description refers to the above-mentioned self-assembly substance formed by HCPs. In addition, the assist probe refers to the probe that can specifically bond to a target analyte to be detected and has the same base sequence partially or entirely with base sequence of one of the above pair of oligonucleotide probes. The assist probe serves for linking the target analyte and the signal probe-polymer.

Patent Document 1: JP 3267576 B

Patent Document 2: JP 3310662 B

Patent Document 3: WO 02/31192

Patent Document 4: JP 2002-355081 A

Patent Document 5: WO 03/029441

DISCLOSURE OF THE INVENTION

Problem to be solved by the Invention

It is an object of the present invention to provide a method of forming a signal probe-polymer capable of forming a polymer efficiently and quantitatively, a signal probe-polymer formed by the method, oligonucleotide probes used in the method, and a method of detecting a target analyte, the method being high in sensitivity and excellent in quantitative capability.

Means for Solving the Problems

The inventors of the present invention have intensively studied to solve the above-mentioned problems so as to enhance detection sensitivity in the detection of the target analyte using a PALSAR method. As a result, the inventors have found the following: the length of a base sequence in each region in HCP is suitably arranged; and guanine or cytosine is used at the terminal of each nucleic acid region if required, whereby a polymer can be formed much more efficiently, and moreover, stability and sensitivity of detection of the target analyte can be remarkably enhanced compared with the case where each region has 20 bases. As a result, the inventors have reached to the present invention.

That is, a method of forming a signal probe-polymer of the present invention comprises: reacting a plurality of pairs of oligonucleotide probes with each other to form a polymer, a first probe of the pair of oligonucleotide probes comprising three nucleic acid regions of X, Y, and Z regions, which are located in the stated order from the 5'-terminal and having a structure represented by the following chemical formula (1); and

[Chemical formula 1]

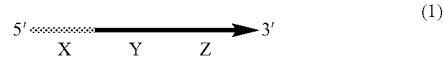

(1)

a second probe of the pair of oligonucleotide probes comprising three nucleic acid regions of X', Y', and Z' regions, which are located in the stated order from the 5'-terminal and having a structure represented by the following chemical formula (2),

[Chemical formula 2]

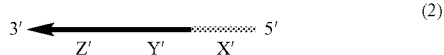

(2)

(in the above chemical formula (1) and chemical formula (2), each of X and X', each of Y and Y', and each of Z and Z' are hybridizable complementary regions), wherein each region of the oligonucleotide probes has a length of from 13 to 15 bases.

In the method of forming a signal probe-polymer of the present invention, each region of the oligonucleotide probes has a length of preferably 14 bases or 15 bases and more preferably 14 bases.

All the bases at both terminals of the respective nucleic acid regions are preferably guanine or cytosine.

Each of the oligonucleotide probes is preferably labeled with a labeling substance. The labeling substance preferably is acridinium ester, a radioactive isotope, biotin, digoxigenin, a fluorescent substance, a luminescent substance, or pigment.

The signal probe-polymer of the present invention is characterized by being formed by the method of forming a signal probe-polymer of the present invention.

The method of detecting a target analyte in a sample of the present invention comprises: forming a polymer by the method of forming a signal probe-polymer of the present invention, and detecting the target analyte by detecting the polymer.

The method of the present invention preferably comprises: providing an assist probe which is specifically bindable with the target analyte and has the same base sequence partially or entirely as the base sequence of one of the pair of oligonucleotide probes; forming a complex including the target analyte, the assist probe and the polymer; and detecting the target analyte by analyzing the complex.

Examples of the target analyte is at least one kind selected from the group consisting of a nucleic acid, an antigen, an antibody, a receptor, a hapten, an enzyme, a protein, a peptide, a polymer, and a glucide.

When the target analyte is a nucleic acid, one of the pair of oligonucleotide probes has preferably a sequence complementary to a part of the sequence of the target nucleic acid (target gene). Moreover, in order to link the target gene to the polymer, it is suitable to use an assist probe having regions each complementary to each of the base sequence of the target gene and the base sequence of one of the pair of oligonucleotide probes.

A pair of oligonucleotide probes of the present invention includes:

a first probe of the pair of oligonucleotide probes comprising three nucleic acid regions of X, Y, and Z regions, which are located in the stated order from the 5'-terminal and having a structure represented by the following chemical formula (1); and

[Chemical formula 3]

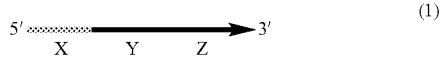

(1)

a second probe of the pair of oligonucleotide probes comprising three nucleic acid regions of X', Y', and Z' regions, which are located in the stated order from the 5'-terminal and having a structure represented by the following chemical formula (2),

[Chemical formula 4]

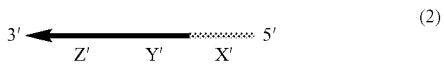

(2)

(in the above chemical formula (1) and chemical formula (2), each of X and X', each of Y and Y', and each of Z and Z' are hybridizable complementary regions), wherein each region of the oligonucleotide probes has a length of from 13 to 15 bases.

Each region of the pair of oligonucleotide probes of the present invention has a length of preferably 14 bases or 15 bases and more preferably 14 bases.

All the bases at both terminals of the respective nucleic acid regions are preferably guanine or cytosine.

Each of the oligonucleotide probes is preferably labeled with a labeling substance. The labeling substance preferably is acridinium ester, a radioactive isotope, biotin, digoxigenin, a fluorescent substance, a luminescent substance, or pigment.

Effects of the Invention

The present invention makes it possible to enhance detection sensitivity of the target analyte easily and remarkably.

DESCRIPTION OF NUMERALS

10: a microplate, 12: a target nucleic acid, 14: a capture probe, 16: an assist probe, 18: a pair of oligonucleotide probes (a pair of HCPs), 18a: a first probe (a first HCP), 18b: a second probe (a second HCP), 20: a self-assembly substance, a signal probe-polymer, 30: s support, 32: a target antigen, 34, 35: an antibody, 36: an assist probe, 38: a complex, 40: a polymer.

BEST MODE FOR CARRYING OUT THE INVENTION

Embodiments of the present invention will be hereinafter described based on the attached drawings. Since the shown examples are just for exemplification, various modifications are of course feasible as long as the modifications do not depart from the technical idea of the present invention.

Figure 1:
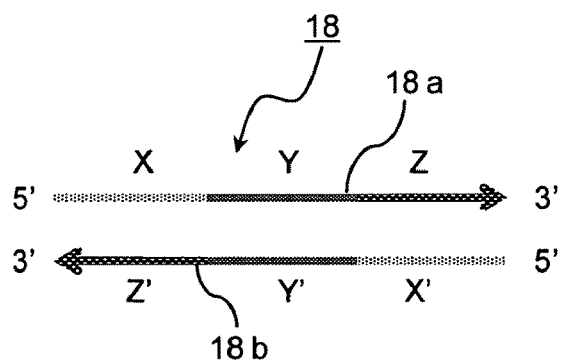
FIG. 1 is a schematic explanatory drawing showing a pair of HCPs.
Figure 2:
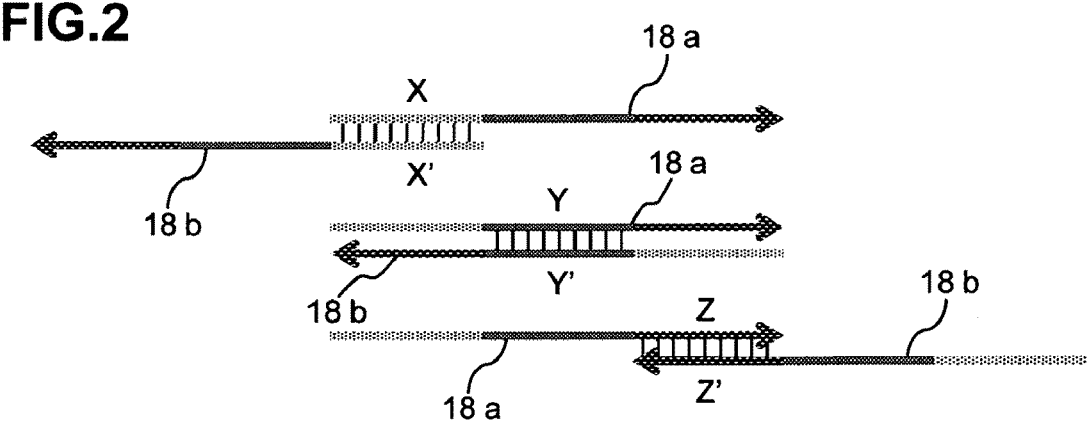
FIG. 2 is a schematic explanatory drawing showing a bonding pattern of the pair of HCPs.
Figure 3:
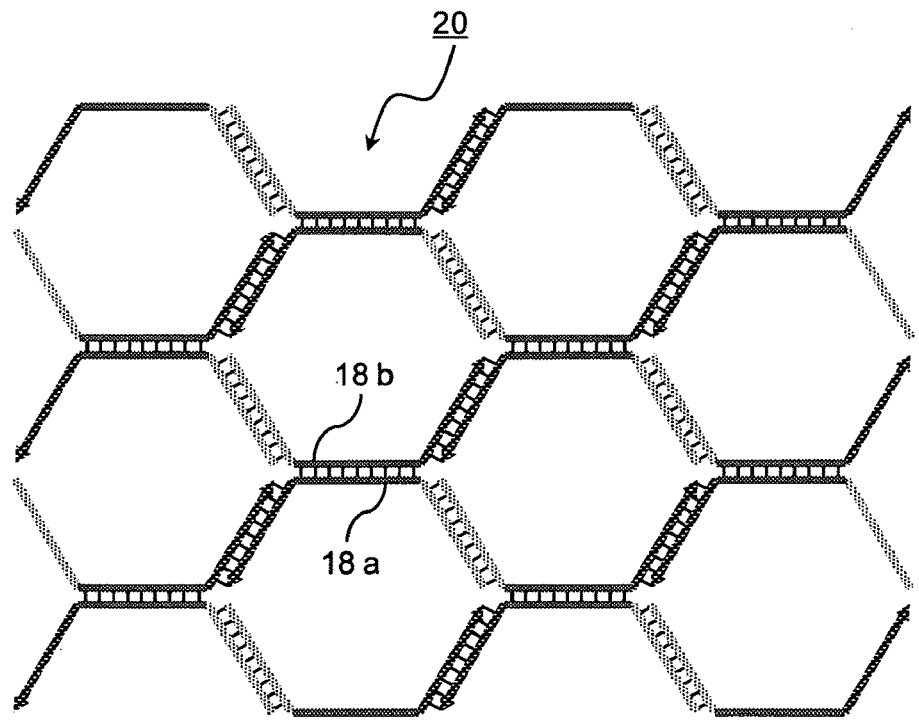
FIG. 3 is a schematic explanatory drawing showing a polymer formed by a plurality of pairs of HCPs.

FIG. 1 is a schematic explanatory drawing showing a pair of oligonucleotide probes (a pair of HCPs). FIG. 2 is a schematic explanatory drawing showing a bonding pattern of the HCPs of FIG. 1. FIG. 3 is a schematic explanatory drawing showing a self-assembly substance formed by a plurality of pairs of HCPs of FIG. 1.

Each of the pair of oligonucleotide probes of the present invention has a feature in that, as shown in FIG. 1, the pair of oligonucleotide probes are a pair of oligonucleotide probes (a pair of HCPs) made up of a first probe (a first HCP) 18a constituted of three nucleic acid regions, the first probe having a nucleic acid region X, a nucleic acid region Y, and a nucleic acid region Z, which are located in the stated order from the 5'-terminal, and a second probe (a second HCP) 18b constituted of three nucleic acid regions, the second probe having a nucleic acid region X', a nucleic acid region Y', and a nucleic acid region Z', which are located in the stated order from the 5'-terminal, and each of the oligonucleotide probes has a length of 13 to 15 bases in each region.

In the pair of HCPs, each of the nucleic acid region X and the nucleic acid region X', each of the nucleic acid region Y and the nucleic acid region Y', and each of the nucleic acid region Z and the nucleic acid region Z' are hybridizable complementary nucleic acid regions. As shown in FIG. 2, the nucleic acid region X and the nucleic acid region X' are bonded with each other, the nucleic acid region Y and the nucleic acid region Y' are bonded with each other, and the nucleic acid region Z and the nucleic acid region Z' are bonded with each other. Each of the pair of HCPs of the present invention has guanine (G) or cytosine (C) at both terminals of each region, and it is preferable that a C—G bonding is formed at the terminal of each region when the pair of HCPs are hybridized.

The length of each region of the HCPs is set to 13 to 15 bases, preferably 14 or 15 bases. The lengths of three regions in a probe may be the same or different from each other. It is more preferable that each of the lengths of the regions in the HCPs be all 14 or 15 bases.

The above oligonucleotide probes are generally constituted of DNA or RNA, and may be constituted of nucleic acid analogs. Examples of the nucleic acid analogs include Peptide Nucleic Acid (PNA, see WO 92/20702 and others) and Locked Nucleic Acid (LNA, see Koshkin AA et al. Tetrahedron 1998. 54, 3607-3630., Koshkin AA et al. J. Am. Chem. Soc. 1998. 120, 13252-13253., Wahlestedt C et al. PNAS. 2000. 97, 5633-5638. and the others). In addition, although a pair of oligonucleotide probes is generally constituted of the same kind of nucleic acids, a DNA probe and an RNA probe may, for example, constitute a pair. That is, kinds of nucleic acids of the probe can be selected from DNA, RNA, and a nucleic acid analog (such as PNA and LNA). Besides, constitution of nucleic acids in one probe is not limited to constitution of one kind of nucleic acid such as only DNA, and, for example, an oligonucleotide probe (chimeric probe) constituted of DNA and RNA can be used as required. Such a chimeric probe is included in the present invention.

Those probes can be synthesized by a known method. In case of DNA probes, for example, probes can be synthesized by a Phosphoamidide method using the DNA synthesizer 394 type manufactured by Applied Biosystems Inc. In addition, a phosphate triester method, an H-phosphonate method, a thiophosphonate method, and the like can be exemplified as other methods, and the probes synthesized by any method can be used.

The method of forming a signal probe-polymer of the present invention is in that the signal probe-polymer is formed by reacting a plurality of pairs of the pair of HCPs of the present invention with each other. As shown in FIG. 3, a hybridization reaction of a plurality of pairs of the pair of HCPs leads to efficient formation of a signal probe-polymer 20, which is a self-assembly substance of HCPs, depending on concentrations of probes.

The number of HCPs to be used is not particularly limited, and the number of HCPs to be used is in the range of $10^2$ to $10^{15}$. Composition and concentration of a reaction buffer solution are not particularly limited, and a common buffer solution to be usually used for amplification of nucleic acids can be suitably used. A usual range of a pH of a reaction buffer solution is suitable, and a reaction buffer solution having a pH in the range of 7.0 to 9.0 can be preferably used. A temperature condition of the hybridization reaction is also not particularly limited, and a usual temperature condition is appropriate. Reaction temperature is preferably 40° C. to 80° C., more preferably 55° C. to 65° C. Moreover, it is preferable that a reaction temperature region is partially formed in a reaction solution, and a self-assembly reaction is performed in the reaction temperature region (WO 2005/106031). Reaction temperature applied in the reaction temperature region partially formed is preferably 40° C. to 80° C. and more preferably 55° C. to 65° C.

Detection of a target analyte by using the method of forming a signal probe-polymer of the present invention contributes to enhance stability and sensitivity of detection of the target analyte.

The method of detecting a target analyte of the present invention is in that a polymer is formed by using the method of forming a signal probe-polymer of the present invention, and the target analyte in a sample is detected by detecting the polymer. Specific examples of the method of detecting a target analyte include: a method in which a complex of a target analyte and a polymer is formed, and the target analyte is detected by detecting the polymer (for example, Patent Document 5); and a method in which a polymer is formed by using a process in which the polymer is formed only in the case where a target analyte is present, and the target analyte is detected by detecting the polymer (for example, WO 02/18642, WO 2004/074480, and WO 2004/072302).

As a sample for measuring a target analyte in the present invention, any sample having a possibility of containing the target analyte can be applied. Examples of the sample include samples derived from living organisms such as blood, serum, urine, feces, cerebrospinal fluid, tissue fluid, sputum, and cell culture and the like, and samples possibly containing or being infected by viruses, bacteria, and molds and the like.

Examples of the target analyte include a nucleic acid, an antigen, an antibody, a receptor, a hapten, an enzyme, a protein, a peptide, a polymer, a glucide, and a combination thereof. The target analyte may be one suitably prepared from a sample or one isolated from a sample. Besides, nucleic acids such as DNA and RNA and the like can also be used, the nucleic acids being obtained by amplifying a target nucleic acid in a sample by a known method. As the target nucleic acid (a target gene), single-strand DNA and/or RNA and double-strand DNA and/or RNA can be used. In addition, SNPs (single nucleotide polymorphism) can be used as the target nucleic acid.

In the detection method of the present invention, there is preferably used an assist probe specifically bindable with the target analyte and having the same nucleic acid region partially or entirely as the nucleic acid region of one of the pair of HCPs of the present invention (that is, a first probe or a second probe). A complex containing a target analyte, the assist probe, and a polymer is formed by using the assist probe, and the target analyte is detected by analyzing the complex, whereby the target analyte can be detected more easily.

The assist probe can be suitably selected depending on a target analyte. For example, when the target analyte is a nucleic acid, it is preferable that an assist probe having a sequence complementary to one region of the target nucleic acid is used to bond with each other through hybridization.

When the target analyte is an antigen, there is preferably used an assist probe obtained by bonding an antibody by chemical bonding such as an assist probe obtained by preliminarily conjugating an antibody by bonding an amino group, a carboxyl group, and the like. There may be also used an assist probe obtained by bonding a biotinylated antibody with streptavidin.

In addition, when the target analyte is a nucleic acid, the target nucleic acid can be detected as follows: one of the pair of HCPs is constituted so as to have the sequence complementary to a part of the sequence of the target nucleic acid; a complex of the target nucleic acid and a polymer is formed by using the pair of HCPs; and the polymer is detected, whereby the target nucleic acid can be detected.

Further, the detection method of the present invention preferably includes a step of capturing a target analyte with a reaction material for detecting the target analyte. The present invention is applicable to various reaction materials for detecting a target analyte, and is suitably used in a DNA chip, a DNA microarray (see Marshall, A., Hodgson, J. DNA chips: an array of possibilities. Nat Biotechnol. 16, 27-31, 1998. and the like), a microplate, a magnetic particle, and the like.

A method of capturing a target analyte with a reaction material is not particularly limited. A method including the following steps is preferable: using a reaction material obtained by bonding a capturing material capable of specifically bonding to a target analyte; and bonding the reaction material and the target analyte by bonding of the capturing material and the target analyte.

The capturing material may be suitably selected depending on a target analyte and is not particularly limited. When the target analyte is a nucleic acid, as the capturing material there is preferably used an oligonucleotide (capture probe) having the base sequence complementary to one region (excluding the region complementary to an assist probe) of the target nucleic acid. When the target analyte is an antigen or an antibody, as the capturing material there is preferably used an antibody or an antigen that specifically bonds to the target analyte. In addition, when the target analyte is a glucide, as the capturing material there is preferably used lectin that specifically bonds to the target analyte.

The method of detecting a target analyte (a target substance) of the present invention will be hereinafter described more specifically by exemplifying the case where a nucleic acid or an antigen is detected as the target analyte (the target substance).

Figure 4:
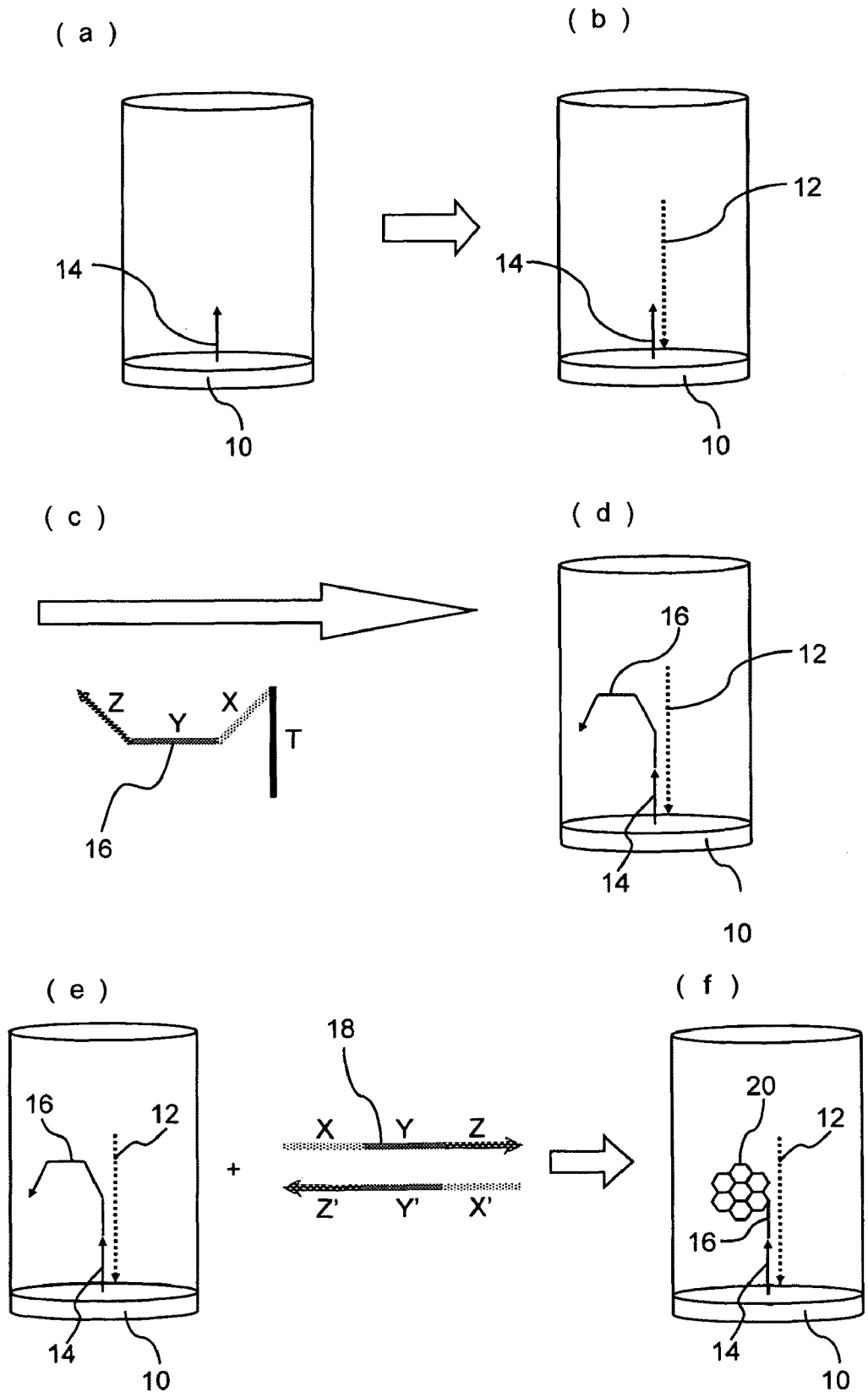
FIG. 4 is a schematic explanatory drawing showing an example of a method of detecting a target nucleic acid using a PALSAR method.

FIG. 4 is a schematic explanatory drawing showing an example of a method of detecting a target nucleic acid using a PALSAR method. In FIG. 4, 10 denotes a microplate as a reaction material, 12 denotes a target nucleic acid, 14 denotes a capture probe having the base sequence complementary to the target nucleic acid, 18 denotes a pair of HCPs [a first HCP (nucleic acid regions of XYZ)] and a second HCP (nucleic acid regions of X'Y'Z')], and 16 denotes an assist probe having the same nucleic acid regions (XYZ) as that of the first HCP and having the nucleic acid region T complementary to that of the target nucleic acid 12.

As shown in FIGS. 4(*a*), 4(*b*), 4(*c*), and 4(*d*), existence of the target nucleic acid in a sample can be confirmed by the following steps: the capture probe 14 immobilized on the microplate 10 and the assist probe 16 are bonded to the target nucleic acid 12; a complex composed of the assist probe 16, the target nucleic acid 12, and the capture probe 14 is formed on the microplate 10; a plurality of pairs of the pair of HCPs 18 are added [FIG. 4(*e*)] to cause a reaction with the assist probe 16, whereby a polymer 20 is formed; the target nucleic acid 12 and the polymer 20 are bonded via the assist probe 16 [FIG. 4(*f*)], and the polymer is analyzed. It should be noted that, in FIG. 4, after the capture probe is reacted with the target nucleic acid [FIG. 4(*b*)], the target nucleic acid is reacted with the assist probe [FIG. 4(*d*)], but the reaction order of the capture probe and the target nucleic acid and the reaction order of the target nucleic acid and the assist probe are not particularly limited. Either of the reactions may be performed earlier, or both reactions may be performed simultaneously.

Figure 5:
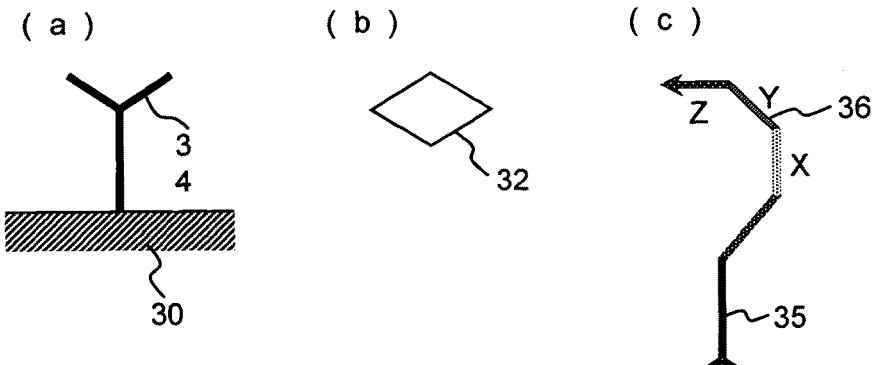
FIG. 5 is a schematic explanatory drawing showing an example of a method of detecting a target antigen using a PALSAR method, in which part (a) shows an antibody bonded to a support, part (b) shows a target antigen, and part (c) shows an assist probe to which an antibody is bonded.
Figure 6:
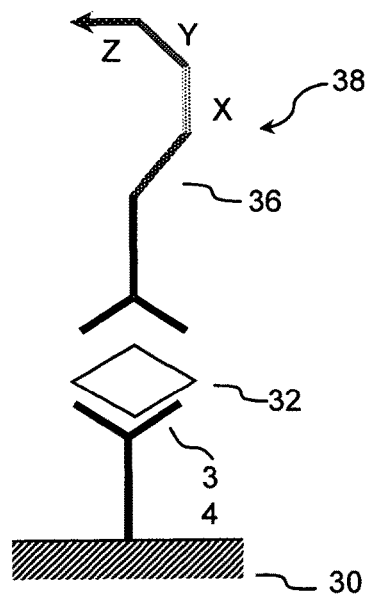
FIG. 6 is a schematic explanatory drawing showing an example of a method of detecting a target antigen using a PALSAR method, the drawing showing a complex including an antibody bonded to a support, a target antigen, and an assist probe to which an antibody is bonded.
Figure 7:
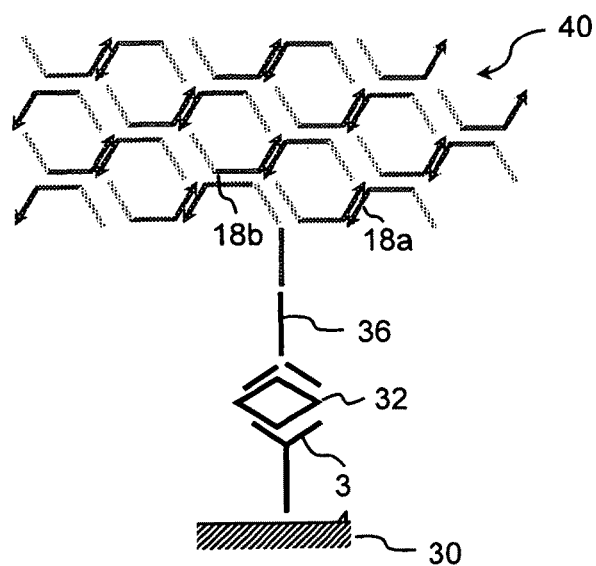
FIG. 7 is a schematic explanatory drawing showing an example of a method of detecting a target antigen using a PALSAR method, the drawing showing a polymer formed on the complex of FIG. 6.

FIGS. 5 to 7 are schematic explanatory drawings showing an example of a method of detecting a target antigen using a PALSAR method, wherein an antibody is used to specifically bond it to the target antigen. In FIGS. 5 to 7, 30 denotes a support, 32 denotes a target antigen, 34 denotes an antibody specific to the target antigen, and 36 denotes an assist probe having the same nucleic acid regions (XYZ) as that of the first HCP, the assist probe being obtained by bonding an antibody 35 specific to the target antigen.

As shown in FIGS. 5 and 6, by a sandwich immunoassay method, both the support 30 on which the antibody 34 is preliminarily immobilized and the antibody 35 included in the assist probe 36 capture the target antigen 32, whereby a complex 38 is formed. After that, a plurality of pairs of HCPs [a first HCP (numeral 18*a*) and a second HCP (numeral 18*b*)] are added, and then, as shown in FIG. 7, the assist probe 36 and a plurality of pairs of HCPs are reacted, whereby a polymer 40 is formed on the complex 38. The polymer is analyzed to confirm the existence of the target nucleic acid in a sample.

In the present invention, a method of detecting a signal probe-polymer is not particularly limited. A method including the following step is preferable: one or both of the pair of oligonucleotide probes (first and second probes) are preliminarily labeled with a labeling substance; and the detection is performed by using the labeling substance. The labeling substance is preferably acridinium ester, a radioactive isotope, biotin, digoxigenin, a fluorescent substance, a luminescent substance, or pigment. Acridinium ester is particularly preferable in consideration of its operability, quantitative capability, and sensitivity. To be specific, one or both of the pair of oligonucleotide probes are preliminarily labeled with a fluorescent substance, and the existence of the polymer can be detected based on a photochemical change of the fluorescent substance. In addition, one or both of the pair of oligonucleotide probes are preliminarily labeled with a chromogenic enzyme or a luminescent enzyme, and the existence of the polymer can be detected based on a photochemical change caused by the chromogenic enzyme or luminescent enzyme. Moreover, one or both of the pair of oligonucleotide probes are preliminarily labeled with a radioactive isotope, and the existence of the polymer can be detected by the radioactive isotope.

Further, the existence of the formed polymer can be detected by hybridizing a labeled probe to the polymer. As the labeled probe, there may be used a substance labeled with a chromogenic enzyme, a luminescent enzyme, a radioactive isotope, or the like. Besides, a fluorescent substance having a characteristic of bonding to a nucleic acid is added to the formed polymer, and the existence of the polymer can be detected based on a photochemical change of the fluorescent substance. As the fluorescent substance, a fluorescent substance having a characteristic of entering a pair of double-strand bases is preferable. Examples of the fluorescent substance preferably include SYBR Green I stain, SYBR Green II stain, SYBR Green Gold stain, Vistra Green stain, Gelstar stain, Radiant Red stain, PicoGreen, RiboGreen, OliGreen, Hoechst33258 (Bis-Benzimide), Propidium Iodide, YO-PRO-1 Iodide, YO-PRO-3 Iodide (all of them are manufactured by Molecular Probes, Inc.), ethidium bromide, Distamycin A, TOTO, Psoralen, acridinium ester, acridinium orange (Acridine Orange), and AOAO (homodimer).

In addition, the polymer of the present invention has a characteristic of expressing a hypochromic effect called "hypochromism" to an extremely large degree, the hypochromism being a phenomenon that the intensity of an absorption band of an ultraviolet portion at 260 nm decreases. Therefore, the state of the polymer can be confirmed by measuring the absorption of the ultraviolet portion at a wavelength of 260 nm.

EXAMPLES

Examples 1 to 7 and Experimental Examples 1 to 6

1. Purpose

In the formation of a polymer by HCPs, formation efficiency of a polymer depending on the difference of the number of bases in each region in HCPs was compared by using HCPs each having various base numbers.

2. Method of Preparing Each Solution (2-1) Preparation of a HCP Solution

As shown in Table 1 and Table 2, each pair of HCPs (a first probe and a second probe) having different base numbers in each region was used in each example, a concentration of each pair of HCPs was adjusted so as to attain an absorbance of 1.2 to 1.5 at 260 nm at the start of a reaction, and each pair of HCPs was dissolved in each of reaction solutions [4×SSC, 0.2% SDS], whereby HCP solutions were prepared. Table 1 shows each number of bases in each region (X-Y-Z) of the HCPs (a first probe and a second probe) used in Examples 1 to 7 and SEQ ID number of base sequence in each probe. Table 2 shows each number of bases in each region (X-Y-Z) of the HCPs (a first probe and a second probe) used in Experimental Examples 1 to 6 and SEQ ID number of base sequence in each probe.

TABLE 1

| HCPs used in Examples 1 to 7 |
| --- |

|  | Example 1 | Example 2 | Example 3 | Example 4 | Example 5 | Example 6 | Example 7 |
| --- | --- | --- | --- | --- | --- | --- | --- |
| Number of bases in each region (X-Y-Z) SEQ ID No. | 13-13-13 | 14-14-14 | 15-15-15 | 14-14-15 | 14-15-14 | 15-15-14 | 15-14-15 |
| First probe | 1 | 3 | 5 | 7 | 9 | 11 | 13 |
| Second probe | 2 | 4 | 6 | 8 | 10 | 12 | 14 |

TABLE 2

| HCPs used in Experimental Examples 1 to 6 |
| --- |

|  | Experimental Example 1 | Experimental Example 2 | Experimental Example 3 | Experimental Example 4 | Experimental Example 5 | Experimental Example 6 |
| --- | --- | --- | --- | --- | --- | --- |
| Number of bases in each region (X-Y-Z) SEQ ID No. | 12-12-12 | 16-16-16 | 17-17-17 | 18-18-18 | 19-19-19 | 20-20-20 |
| First probe | 15 | 17 | 19 | 21 | 23 | 25 |
| Second probe | 16 | 18 | 20 | 22 | 24 | 26 |

(2-2) Preparation of a Control Solution

For the purpose of comparing formation efficiency of a polymer, each of solutions having only the first probe added (the concentration of the first probe: twice the volume of the first probe added in the above-mentioned HCP solution) was prepared for each of Examples and Experimental Examples. Each of them serves as a control.

3. Reaction

100 µL each of the prepared HCP solutions were fed into each of 0.2 mL tubes. The solution was heated at 94° C. for 1 minute and immediately cooled on ice. Next, in order that the temperature of the HCP solution cooled on ice does not reach the temperature higher than the predetermined temperature, the tube was preliminarily set at the state where the temperature of the tube reached at each reaction temperature (55.0, 56.2, 57.5, 59.2, 61.4, 63.9, 66.1, 67.7, 68.9, or 70.0° C.) to undergo an reaction for 2 hours. After the reaction, the HCP solution was stored at 28° C. in order to prevent the HCP solution from becoming cloudy owing to SDS in the HCP solution. The following analysis was performed. Further, the same experiment was performed on the prepared control solution described above in the same manner as that for the HCP solution.

4. Analysis (4-1) Measurement of Absorbance

Figure 8:
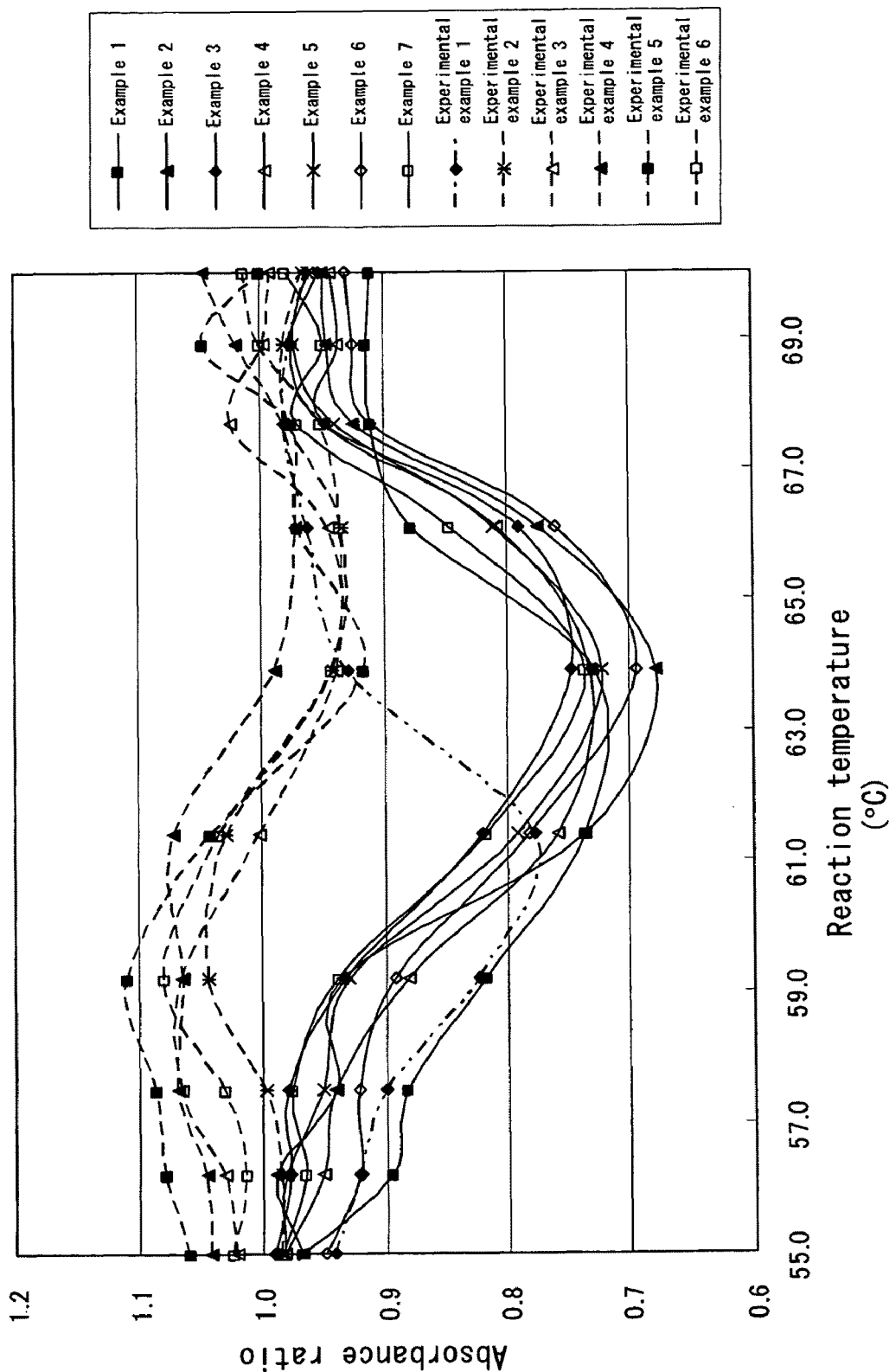
FIG. 8 is a graph showing results of absorbance measurement in Examples 1 to 7 and Experimental Examples 1 to 6.

Absorbance of the HCP solution and the control solution after the reaction was measured at a wavelength of 260 nm. Each absorption ratio of a HCP solution to a control at each reaction temperature was calculated. Each absorption ratio of the HCP solution to the control at each reaction temperature is shown in Table 3 and Table 4. FIG. 8 is a graph showing each absorption ratio at each reaction temperature.

polymer and an indicator of a high degree of structure regularity in the polymer. The above results indicated the following. HCPs each composed of only 13, 14, 15 bases and a mixture of 14 and 15 bases in each region showed high formation efficiency of polymers. Out of those, HCPs each composed of only 14 bases in each region and showing a remarkable degree of hypochromism showed particularly high formation efficiency of regularly-arranged polymers.

(4-2) Electrophoresis

Figure 9:
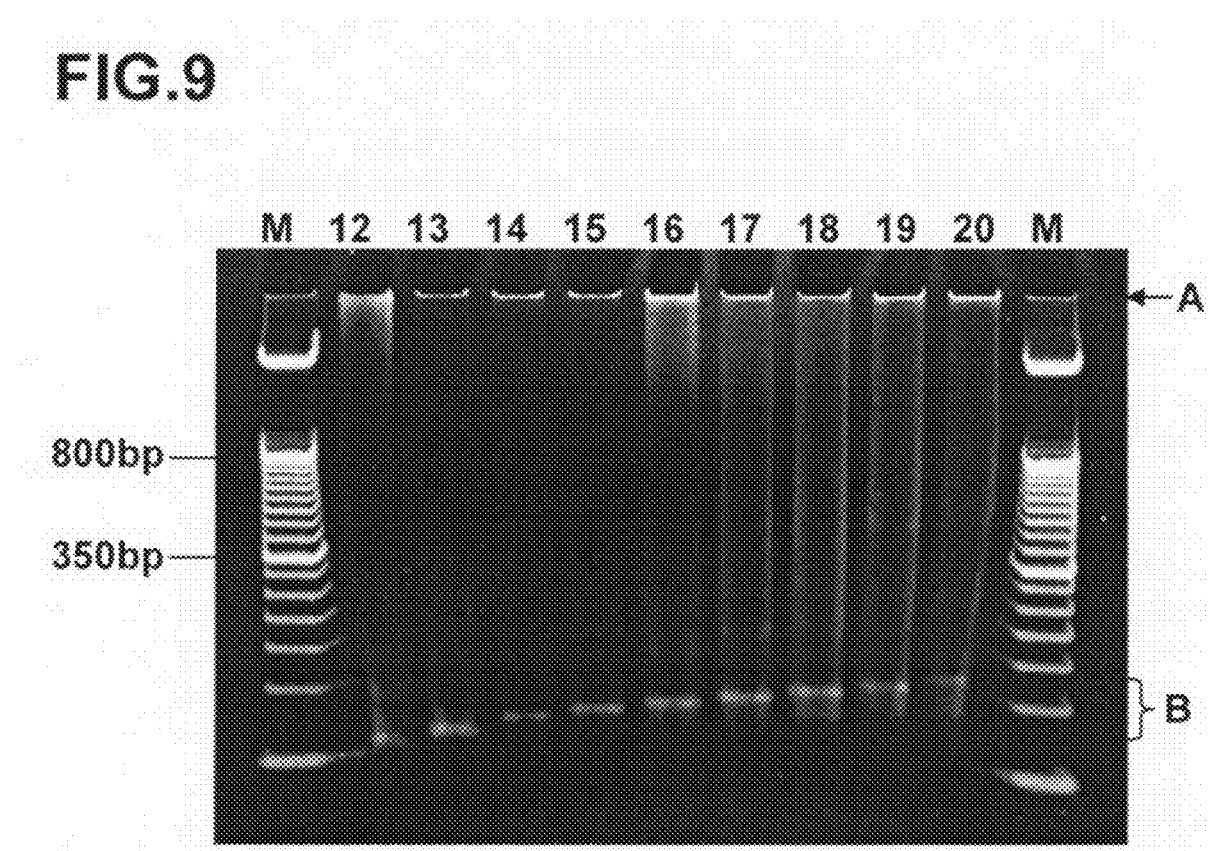
FIG. 9 is a photo showing results of electrophoresis in Examples 1 to 3 and Experimental Examples 1 to 6.
Figure 10:
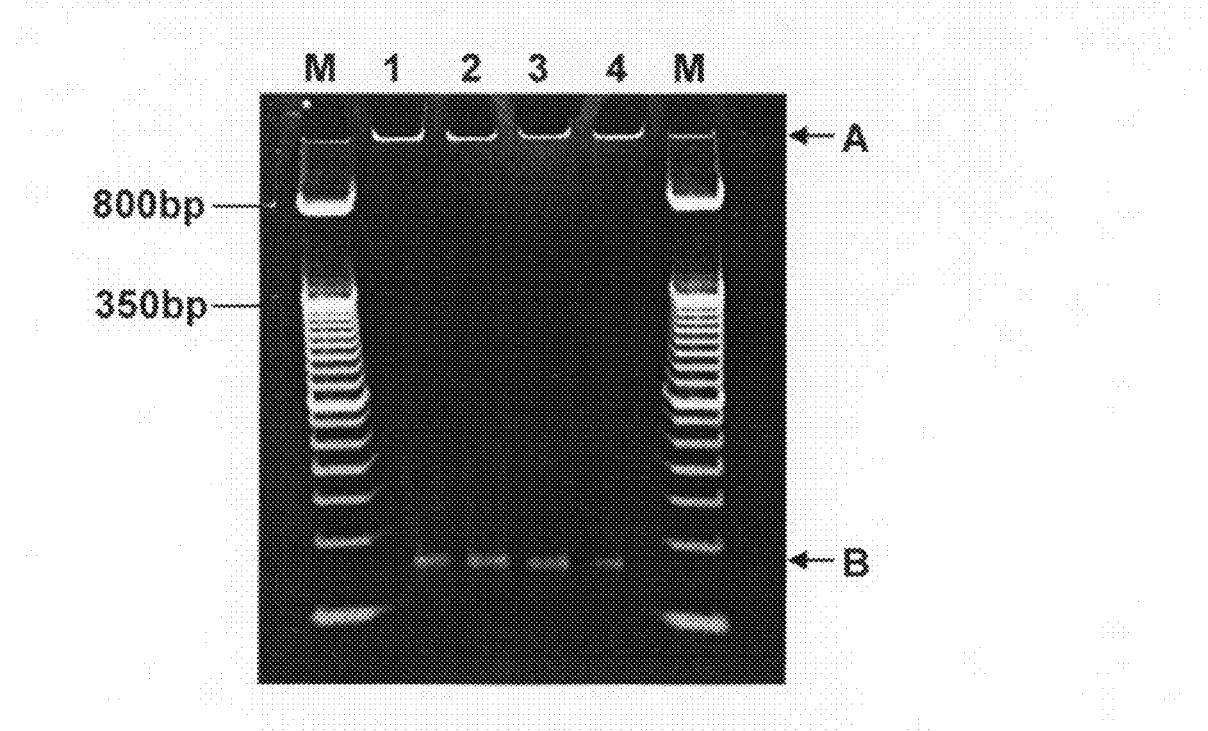
FIG. 10 is a photo showing results of electrophoresis in Examples 4 to 7.

Samples (samples shown in Table 3 and Table 4) having a temperature at which hypochromism was exhibited were confirmed by 6% polyacrylamide gel electrophoresis. FIG. 9 is a photo showing the results of electrophoresis in Examples 1 to 3 and Experimental Examples 1 to 6. In FIG. 9, each lane number denotes the number of bases in each region, lanes 13 to 15 denote samples of Examples 1 to 3, lane 12 and lanes 16 to 20 denotes samples of Experimental Examples 1 to 6, and lane M denotes a molecular size marker. FIG. 10 is a photo

TABLE 3

| Temperature (° C.) | Example 1 | Example 2 | Example 3 | Example 4 | Example 5 | Example 6 | Example 7 |
|---|---|---|---|---|---|---|---|
| 55.0 | 0.968 | 0.970 | 0.991 | 0.983 | 0.983 | 0.950 | 0.984 |
| 56.2 | 0.895 | 0.989 | 0.979 | 0.952 | 0.982 | 0.923 | 0.966 |
| 57.5 | 0.883 | 0.941 | 0.980 | 0.943 | 0.952 | 0.922 | 0.977 |
| 59.2 | 0.818*[1] | 0.936*[1] | 0.932*[1] | 0.880*[1] | 0.930*[1] | 0.893*[1] | 0.940*[1] |
| 61.4 | 0.736 | 0.737 | 0.819 | 0.759 | 0.792 | 0.783 | 0.817 |
| 63.9 | 0.729*[2] | 0.679*[2] | 0.748*[2] | 0.732*[2] | 0.723*[2] | 0.694*[2] | 0.736*[2] |
| 66.1 | 0.877 | 0.775 | 0.790 | 0.808 | 0.810 | 0.759 | 0.847 |
| 67.7 | 0.910 | 0.924 | 0.948 | 0.948 | 0.941 | 0.911 | 0.970 |
| 68.9 | 0.914 | 0.947 | 0.975 | 0.938 | 0.974 | 0.925 | 0.950 |
| 70.0 | 0.910 | 0.950 | 0.953 | 0.944 | 0.961 | 0.931 | 0.980 |

*[1] a sample used in electrophoresis
*[2] a sample showing the lowest ratio in each example

TABLE 4

| Temperature (° C.) | Experimental Example 1 | Experimental Example 2 | Experimental Example 3 | Experimental Example 4 | Experimental Example 5 | Experimental Example 6 |
|---|---|---|---|---|---|---|
| 55.0 | 0.942 | 0.985 | 1.021 | 1.042 | 1.059 | 1.024 |
| 56.2 | 0.921 | 0.984 | 1.031 | 1.045 | 1.077 | 1.014 |
| 57.5 | 0.900*[1] | 0.997 | 1.065 | 1.069 | 1.085 | 1.030 |
| 59.2 | 0.822 | 1.043*[1] | 1.066*[1] | 1.063 | 1.109*[1] | 1.079 |
| 61.4 | 0.778*[2] | 1.030 | 1.002 | 1.071*[1] | 1.042 | 1.035*[1] |
| 63.9 | 0.929 | 0.942 | 0.939*[2] | 0.990 | 0.918*[2] | 0.945 |
| 66.1 | 0.963 | 0.935*[2] | 0.946 | 0.973*[2] | 0.971 | 0.936*[2] |
| 67.7 | 0.981 | 0.977 | 1.024 | 0.981 | 0.976 | 0.952 |
| 68.9 | 0.978 | 0.982 | 0.997 | 1.019 | 1.046 | 1.001 |
| 70.0 | 0.963 | 0.966 | 0.993 | 1.047 | 1.000 | 1.013 |

*[1] a sample used in electrophoresis
*[2] a sample showing the lowest ratio in each experimental example As shown in Table 3 and Table 4, Examples 1 to 7, in which HCPs each composed of only 13 bases in each region, HCPs each composed of only 14 bases in each region, HCPs each composed of only 15 bases in each region, and HCPs each composed of a mixture of 14 and 15 bases in each region were used, showed smaller absorbance ratios compared with those shown by the Experimental Examples 1 to 6, in which HCPs each composed of only 12, 16, 17, 18, 19 or 20 bases in each region were used. In particular, the case where HCPs each composed of only 14 bases in each region were used showed the smallest ratio.

Nucleic acids exhibit a phenomenon called "hypochromism" that absorption intensity decreases since the nucleic acids have a regular higher-order structure. That is, comparing each change in absorbance ratios as hypochromism serves as an indicator of formation efficiency of a showing the results of electrophoresis in Examples 4 to 7. Lanes 1 to 4 denote respective samples of Examples 6, 7, 4, and 5, and lane M denotes a molecular size marker. In addition, A denotes each band of polymers in FIGS. 9 and 10, and B denotes each band of unreacted probes in FIGS. 9 and 10.

As shown in FIGS. 9 and 10, Examples 1 to 7, in which HCPs each composed of only 13, 14, 15 bases and a mixture of 14 and 15 bases in each region were used, showed a smaller amount of ladder bands at the upper portion of each lane, a smaller number of unreacted probes (B in FIGS. 9 and 10) at the lower portion of each lane, and higher formation efficiency of polymers, compared with Experimental Examples 1 to 6, in which HCPs each composed of only 12, 16, 17, 18, 19 or 20 bases in each region were used. In particular, when HCPs each composed of only 14 bases in each region were used, the amount of ladder bands and the number of unreacted probes were smallest. In that case, most HCPs subjected to a reaction were probably related to an efficient self-assembly reaction. As a result, there was shown the fact that formation efficiency of regularly-arranged polymers was particularly high.

Examples 8 to 11 and Experimental Examples 7 to 12

1. Purpose

In the detection of a target gene using the formation of a polymer by HCPs, detection efficiency of the target gene depending on the difference of the number of bases in each region in HCPs was compared by using HCPs each having various numbers of bases.

2. Preparation of Microplate

Each of capture probes (SEQ ID No. 28) was immobilized on a 96-well microplate of strip well-type and used for the experiment, the capture probes each having the sequence complementary to the sequence of the target oligo DNA (SEQ ID No. 27) having the same base sequence as that of rRNA of *Staphylococcus aureus*.

3. Method of Preparing Each Solution (3-1) Preparation of a First Hybridization Probe Solution
Assist probes shown in Table 5 and Table 6 were dissolved in a first hybridization solution [4×SSC, 0.2% SDS, 1% Blocking reagent (manufactured by Roche Applied Science), 20% formamide, Salmon sperm DNA (10 μg/mL)] so that a solution having a concentration of 24 μmol/mL was obtained. The obtained solution served as a first hybridization probe solution to be used for hybridization of the target rRNA and the capture probe. It should be noted that the used assist probe had the same base sequence as that of the first probe and another base sequence complementary to that of the target oligo DNA.

(3-2) Preparation of a Second Hybridization HCP Solution
A pair of HCPs (a first probe and a second probe) each having different numbers of bases in each region and each labeled with DIG at the 5'-terminal as shown in Table 5 and Table 6 were dissolved in a second hybridization solution [4×SSC, 0.2% SDS, 1% Blocking reagent (manufactured by Roche Applied Science)] so that a HCP solution having a concentration of 500 μmol/mL was obtained. The obtained solution served as a second hybridization HCP solution. Table 5 shows the numbers of bases in each region (X-Y-Z) in HCPs (a first probe and a second probe) used in Examples 8 to 11 and SEQ ID number of base sequences in each probe. Table 6 shows the numbers of bases in each region (X-Y-Z) in HCPs (a first probe and a second probe) used in Experimental Examples 7 to 12 and SEQ ID number of base sequences in each probe.

TABLE 5

| HCPs and assist probes used in Examples 8 to 11 | | | | |
|---|---|---|---|---|
| | Example 8 | Example 9 | Example 10 | Example 11 |
| HCP | | | | |
| Number of base in each region (X-Y-Z) | 13-13-13 | 14-14-14 | 15-15-15 | 14-15-14 |
| SEQ ID No. | | | | |
| First probe | 39 | 41 | 43 | 45 |
| Second probe | 40 | 42 | 44 | 46 |
| Assist probe | | | | |
| SEQ ID No. | 29 | 30 | 31 | 32 |

TABLE 6

| HCPs and assist probes used in Experimental Examples 7 to 12 | | | | | | |
|---|---|---|---|---|---|---|
| | Experimental Example 7 | Experimental Example 8 | Experimental Example 9 | Experimental Example 10 | Experimental Example 11 | Experimental Example 12 |
| HCP | | | | | | |
| Number of base in each region (X-Y-Z) | 12-12-12 | 16-16-16 | 17-17-17 | 18-18-18 | 19-19-19 | 20-20-20 |
| SEQ ID No. | | | | | | |
| First probe | 47 | 49 | 51 | 53 | 55 | 57 |
| Second probe | 48 | 50 | 52 | 54 | 56 | 58 |
| Assist probe | | | | | | |
| SEQ ID No. | 33 | 34 | 35 | 36 | 37 | 38 |

4. Reaction (4-1) First Hybridization
To the prepared 96-well microplate of strip well type, 50 μL each of the target oligo DNAs (SEQ ID No. 27) each having different concentrations (0.05, 0.1, 0.5, 1, or 10 fmol/mL) and 50 μL each of the first hybridization probe solution were fed. The microplate was tightly sealed with a plate-sealer, and then was subjected to a reaction for 1 hour under a condition of at 20° C. in the upper part of the microplate and at 45° C. in the lower part of the microplate. After the reaction, the microplate was washed with a washing solution (50 mM-Tris, 0.3 M-NaCl, 0.01%-TritonX-100, pH 7.6)

(4-2) Second Hybridization (Polymer Formation Reaction by HCP)
After the washing, the washing solution was fully removed from the 96-well microplate. To the microplate, 100 μL each of the second hybridization HCP solution were fed, and the microplate was tightly sealed with a plate-sealer. The microplate was subjected to a reaction for 30 minutes under a condition of at 20° C. in the upper part of the microplate and at 55° C. in the lower part of the microplate.

5. Detection

After the microplate wells were washed, 100 μL of 15 mU/mL ALP-labeled anti-digoxigenin (100 mM Tris, pH 7.5) were added thereto, and the resultant was reacted in an incubator at 37° C. After the microplate wells were washed with a washing solution, 100 μL of a luminescent substrate solution (CDP-Star, manufactured by Tropix, Inc.) were added thereto, and the mixture was reacted for 20 minutes in the dark place. After that, Relative Light Unit (RLU) was measured with a luminometer (Centro LB960, manufactured by BERTHOLD TECHNOLOGIES GmbH & Co KG). The results are shown in Table 7 and FIG. 11.

TABLE 7

| Concentration of Target | Example Number | | | | Experimental Example Number | | | | | |
|---|---|---|---|---|---|---|---|---|---|---|
| (fmol/mL) | 8 | 9 | 10 | 11 | 7 | 8 | 9 | 10 | 11 | 12 |
| 0.05 | 219 | 315 | 246 | 159 | 92 | 127 | 118 | 179 | 141 | 185 |
| 0.1 | 430 | 603 | 453 | 426 | 97 | 266 | 269 | 361 | 299 | 366 |
| 0.5 | 1909 | 2904 | 1941 | 2162 | 175 | 1410 | 1515 | 1743 | 1472 | 1747 |
| 1 | 3903 | 5768 | 4077 | 3935 | 359 | 2860 | 3242 | 3218 | 2897 | 3430 |
| 10 | 34025 | 48548 | 34289 | 37571 | 3312 | 24615 | 28633 | 29492 | 26250 | 30263 |

Figure 11:
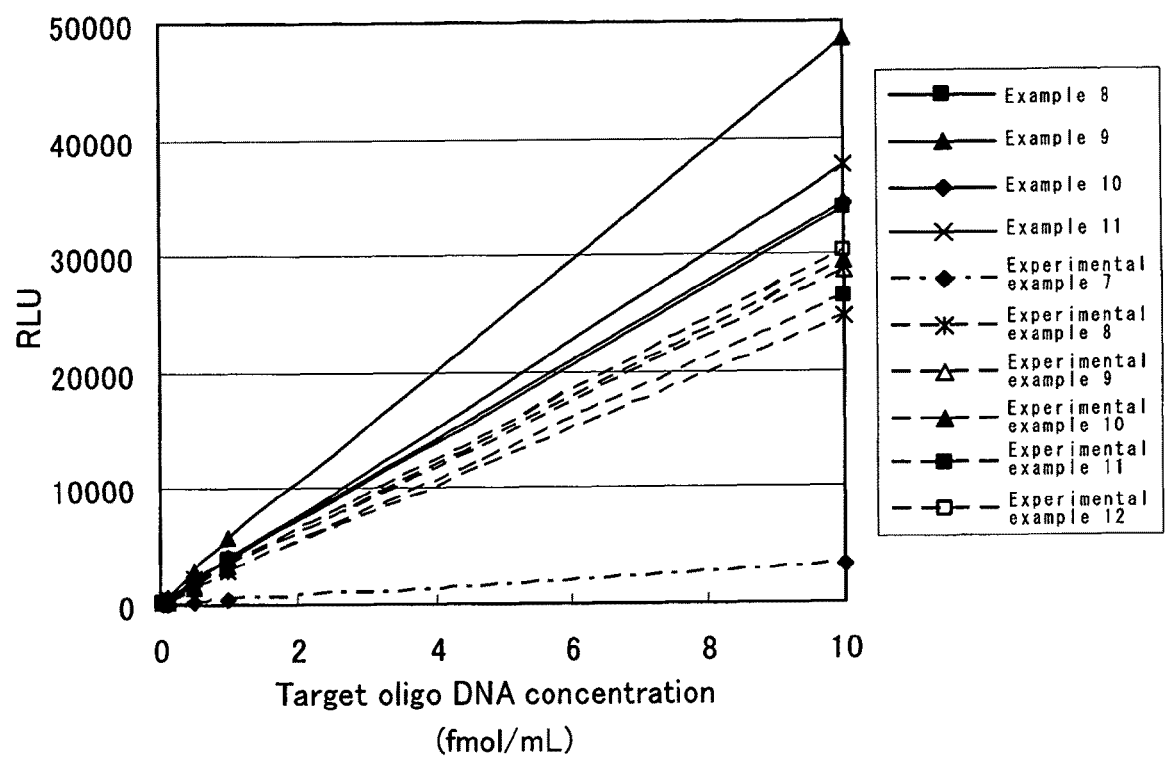
FIG. 11 is a graph showing results of Examples 8 to 11 and Experimental Examples 7 to 12.

As shown in Table 7 and FIG. 11, in Examples 8 to 11, in which HCPs each composed of only 13, 14, 15 bases and a mixture of 14 and 15 bases in each region were used, higher measurements were obtained compared with those obtained in Experimental Examples 7 to 12, in which HCPs each composed of only 12, 16, 17, 18, 19 and 20 bases in each region were used.

The invention claimed is:

1. A method of forming a signal probe-polymer comprising:
reacting a plurality of pairs of oligonucleotide probes with each other to form a polymer,
a first probe of the pair of oligonucleotide probes comprising three nucleic acid regions of X, Y, and Z regions, which are located in the stated order from the 5'-terminal and having a structure represented by the following chemical formula (1); and

[Chemical formula 1]

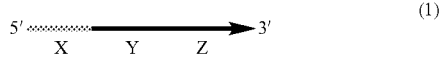

(1)

a second probe of the pair of oligonucleotide probes comprising three nucleic acid regions of X', Y', and Z' regions, which are located in the stated order from the 5'-terminal and having a structure represented by the following chemical formula (2),

[Chemical formula 2]

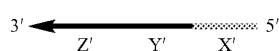

(2)

(in the above chemical formulae (1) and (2), each of X and X', each of Y and Y', and each of Z and Z' are hybridizable complementary regions),
wherein each region of the oligonucleotide probes has a length of from 13 to 15 bases.

2. A method of forming a signal probe-polymer according to claim 1, wherein each region of the oligonucleotide probes has a length of 14 bases or 15 bases.

3. A method of forming a signal probe-polymer according to claim 1, wherein all each region of the oligonucleotide probes has a length of 14 bases.

4. A method of forming a signal probe-polymer according to claim 1, wherein all the bases at both terminals of the respective nucleic acid region are guanine or cytosine.

5. A method of forming a signal probe-polymer according to claim 1, wherein each of the oligonucleotide probes is labeled with a labeling substance.

6. A method of forming a signal probe-polymer according to claim 5, wherein the labeling substance is acridinium ester, a radioactive isotope, biotin, digoxigenin, a fluorescent substance, a luminescent substance, or pigment.

7. A signal probe-polymer which is formed by the method according claim 1.

8. A method of detecting a target analyte in a sample comprising:
forming a polymer by the method according to claim 1, and detecting the target analyte by detecting the polymer.

9. A method of detecting a target analyte according to claim 8, comprising:
providing an assist probe which is specifically bindable with the target analyte and has the same base sequence partially or entirely as the base sequence of one of the pair of oligonucleotide probes;
forming a complex including the target analyte, the assist probe and the polymer; and
detecting the target analyte by analyzing the complex.

10. A method of detecting a target analyte according to claim 8, wherein the target analyte is a nucleic acid, and one of the pair of oligonucleotide probes has a sequence complementary to a part of the sequence of the target nucleic acid.

11. A method of detecting a target analyte according to claim 8, wherein the target analyte is at least one kind selected from the group consisting of a nucleic acid, an antigen, an antibody, a receptor, a hapten, an enzyme, a protein, a peptide, a polymer, and a glucide.

12. A pair of oligonucleotide probes,
a first probe of the pair of oligonucleotide probes comprising three nucleic acid regions of X, Y, and Z regions, which are located in the stated order from the 5'-terminal and having a structure represented by the following chemical formula (1); and

[Chemical formula 3]

$$\begin{array}{ccc} 5' \longrightarrow & & 3' \\ X & Y & Z \end{array} \quad (1)$$

a second probe of the pair of oligonucleotide probes comprising three nucleic acid regions of X', Y', and Z' regions, which are located in the stated order from the 5'-terminal and having a structure represented by the following chemical formula (2),

[Chemical formula 4]

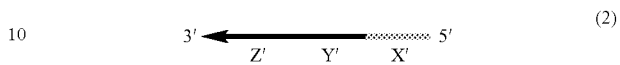
$$\begin{array}{ccc} 3' \longleftarrow & & 5' \\ Z' & Y' & X' \end{array} \quad (2)$$

(in the above chemical formula (1) and chemical formula (2), each of X and X', each of Y and Y', and each of Z and Z' are hybridizable complementary regions),
wherein each region of the oligonucleotide probes has a length of from 13 to 15 bases.

13. A pair of oligonucleotide probes according to claim 12, wherein each region of the oligonucleotide probes has a length of 14 bases or 15 bases.

14. A pair of oligonucleotide probes according to claim 12, wherein all each region of the oligonucleotide probes has a length of 14 bases.

15. A pair of oligonucleotide probes according to claim 12, wherein all the bases at both terminals of the respective nucleic acid region are guanine or cytosine.

16. A pair of oligonucleotide probes according to claim 12, wherein each of the oligonucleotide probes is labeled with a labeling substance.

17. A pair of oligonucleotide probes according to claim 16, wherein the labeling substance is acridinium ester, a radioactive isotope, biotin, digoxigenin, a fluorescent substance, a luminescent substance, or pigment.

\* \* \* \* \*

SEQUENCE LISTING

<160> NUMBER OF SEQ ID NOS: 58

<210> SEQ ID NO 1
<211> LENGTH: 39
<212> TYPE: DNA
<213> ORGANISM: Artificial
<220> FEATURE:
<223> OTHER INFORMATION: Description of Artificial Sequence; Synthetic

<400> SEQUENCE: 1
catctctgct gcccccattc acaccgttc gcctttccg                39

<210> SEQ ID NO 2
<211> LENGTH: 39
<212> TYPE: DNA
<213> ORGANISM: Artificial
<220> FEATURE:
<223> OTHER INFORMATION: Description of Artificial Sequence; Synthetic

<400> SEQUENCE: 2
ggcagcagag atggggtgtg aatgggcgga aaggcgaac                39

<210> SEQ ID NO 3
<211> LENGTH: 42
<212> TYPE: DNA
<213> ORGANISM: Artificial
<220> FEATURE:
<223> OTHER INFORMATION: Description of Artificial Sequence; Synthetic

<400> SEQUENCE: 3
catctctgct ggtcccacat tcacaccgt tcgccataga cg                42

<210> SEQ ID NO 4
<211> LENGTH: 42

```
<212> TYPE: DNA
<213> ORGANISM: Artificial
<220> FEATURE:
<223> OTHER INFORMATION: Description of Artificial Sequence; Synthetic

<400> SEQUENCE: 4
gaccagcaga gatggggtgt gaatgtggcg tctatggcga ac                          42

<210> SEQ ID NO 5
<211> LENGTH: 45
<212> TYPE: DNA
<213> ORGANISM: Artificial
<220> FEATURE:
<223> OTHER INFORMATION: Description of Artificial Sequence; Synthetic

<400> SEQUENCE: 5
cattctctgc tggtcccaca ttcaacaccc gttcgccata gacag                       45

<210> SEQ ID NO 6
<211> LENGTH: 45
<212> TYPE: DNA
<213> ORGANISM: Artificial
<220> FEATURE:
<223> OTHER INFORMATION: Description of Artificial Sequence; Synthetic

<400> SEQUENCE: 6
gaccagcaga gaatggggtg ttgaatgtgg ctgtctatgg cgaac                       45

<210> SEQ ID NO 7
<211> LENGTH: 43
<212> TYPE: DNA
<213> ORGANISM: Artificial
<220> FEATURE:
<223> OTHER INFORMATION: Description of Artificial Sequence; Synthetic

<400> SEQUENCE: 7
catctctgct ggtcccacat tcacacccgt tcgccataga cag                         43

<210> SEQ ID NO 8
<211> LENGTH: 43
<212> TYPE: DNA
<213> ORGANISM: Artificial
<220> FEATURE:
<223> OTHER INFORMATION: Description of Artificial Sequence; Synthetic

<400> SEQUENCE: 8
gaccagcaga gatggggtgt gaatgtggct gtctatggcg aac                         43

<210> SEQ ID NO 9
<211> LENGTH: 43
<212> TYPE: DNA
<213> ORGANISM: Artificial
<220> FEATURE:
<223> OTHER INFORMATION: Description of Artificial Sequence; Synthetic

<400> SEQUENCE: 9
catctctgct ggtcccacat tcaacacccg ttcgccatag acg                         43

<210> SEQ ID NO 10
<211> LENGTH: 43
<212> TYPE: DNA
<213> ORGANISM: Artificial
<220> FEATURE:
<223> OTHER INFORMATION: Description of Artificial Sequence; Synthetic

<400> SEQUENCE: 10
gaccagcaga gatggggtgt tgaatgtggc gtctatggcg aac                         43
```

<210> SEQ ID NO 11
<211> LENGTH: 44
<212> TYPE: DNA
<213> ORGANISM: Artificial
<220> FEATURE:
<223> OTHER INFORMATION: Description of Artificial Sequence; Synthetic

<400> SEQUENCE: 11
cattctctgc tggtcccaca ttcaacaccc gttcgccata gacg              44

<210> SEQ ID NO 12
<211> LENGTH: 44
<212> TYPE: DNA
<213> ORGANISM: Artificial
<220> FEATURE:
<223> OTHER INFORMATION: Description of Artificial Sequence; Synthetic

<400> SEQUENCE: 12
gaccagcaga gaatggggtg ttgaatgtgg cgtctatggc gaac              44

<210> SEQ ID NO 13
<211> LENGTH: 44
<212> TYPE: DNA
<213> ORGANISM: Artificial
<220> FEATURE:
<223> OTHER INFORMATION: Description of Artificial Sequence; Synthetic

<400> SEQUENCE: 13
cattctctgc tggtcccaca ttcacacccg ttcgccatag acag              44

<210> SEQ ID NO 14
<211> LENGTH: 44
<212> TYPE: DNA
<213> ORGANISM: Artificial
<220> FEATURE:
<223> OTHER INFORMATION: Description of Artificial Sequence; Synthetic

<400> SEQUENCE: 14
gaccagcaga gaatggggtg tgaatgtggc tgtctatggc gaac              44

<210> SEQ ID NO 15
<211> LENGTH: 36
<212> TYPE: DNA
<213> ORGANISM: Artificial
<220> FEATURE:
<223> OTHER INFORMATION: Description of Artificial Sequence; Synthetic

<400> SEQUENCE: 15
cactctgctc gccccttcac acccgttcgc cttccg                      36

<210> SEQ ID NO 16
<211> LENGTH: 36
<212> TYPE: DNA
<213> ORGANISM: Artificial
<220> FEATURE:
<223> OTHER INFORMATION: Description of Artificial Sequence; Synthetic

<400> SEQUENCE: 16
gcgagcagag tggggtgtga agggcggaag gcgaac                      36

<210> SEQ ID NO 17
<211> LENGTH: 48
<212> TYPE: DNA
<213> ORGANISM: Artificial
<220> FEATURE:
<223> OTHER INFORMATION: Description of Artificial Sequence; Synthetic

```
<400> SEQUENCE: 17
cattctctgc tgagtcccac attcaacacc tcgttctgcc atagacag            48

<210> SEQ ID NO 18
<211> LENGTH: 48
<212> TYPE: DNA
<213> ORGANISM: Artificial
<220> FEATURE:
<223> OTHER INFORMATION: Description of Artificial Sequence; Synthetic

<400> SEQUENCE: 18
gactcagcag agaatggagg tgttgaatgt ggctgtctat ggcagaac            48

<210> SEQ ID NO 19
<211> LENGTH: 51
<212> TYPE: DNA
<213> ORGANISM: Artificial
<220> FEATURE:
<223> OTHER INFORMATION: Description of Artificial Sequence; Synthetic

<400> SEQUENCE: 19
cattctctgc tgtagtccca cattcaacac actcgttctg cacatagaca g         51

<210> SEQ ID NO 20
<211> LENGTH: 51
<212> TYPE: DNA
<213> ORGANISM: Artificial
<220> FEATURE:
<223> OTHER INFORMATION: Description of Artificial Sequence; Synthetic

<400> SEQUENCE: 20
gactacagca gagaatggag tgtgttgaat gtggctgtct atgtgcagaa c         51

<210> SEQ ID NO 21
<211> LENGTH: 54
<212> TYPE: DNA
<213> ORGANISM: Artificial
<220> FEATURE:
<223> OTHER INFORMATION: Description of Artificial Sequence; Synthetic

<400> SEQUENCE: 21
cattctactg ctgtagtccc acattcatac acactcgttc tgcatcatag acag      54

<210> SEQ ID NO 22
<211> LENGTH: 54
<212> TYPE: DNA
<213> ORGANISM: Artificial
<220> FEATURE:
<223> OTHER INFORMATION: Description of Artificial Sequence; Synthetic

<400> SEQUENCE: 22
gactacagca gtagaatgga gtgtgtatga atgtggctgt ctatgatgca gaac      54

<210> SEQ ID NO 23
<211> LENGTH: 57
<212> TYPE: DNA
<213> ORGANISM: Artificial
<220> FEATURE:
<223> OTHER INFORMATION: Description of Artificial Sequence; Synthetic

<400> SEQUENCE: 23
cattctactg actgtagtcc cacattcata tcacactcgt tctgacatca tagacag   57

<210> SEQ ID NO 24
<211> LENGTH: 57
```

```
<212> TYPE: DNA
<213> ORGANISM: Artificial
<220> FEATURE:
<223> OTHER INFORMATION: Description of Artificial Sequence; Synthetic

<400> SEQUENCE: 24
cattctactg actgtagtcc cacattcata tcacactcgt tctgacatca tagacag        57

<210> SEQ ID NO 25
<211> LENGTH: 60
<212> TYPE: DNA
<213> ORGANISM: Artificial
<220> FEATURE:
<223> OTHER INFORMATION: Description of Artificial Sequence; Synthetic

<400> SEQUENCE: 25
cattctactg actgtagttc cacacattca tatcacactc gttctgacat catagacaag     60

<210> SEQ ID NO 26
<211> LENGTH: 60
<212> TYPE: DNA
<213> ORGANISM: Artificial
<220> FEATURE:
<223> OTHER INFORMATION: Description of Artificial Sequence; Synthetic

<400> SEQUENCE: 26
gaactacagt cagtagaatg gagtgtgata tgaatgtgtg cttgtctatg atgtcagaac     60

<210> SEQ ID NO 27
<211> LENGTH: 105
<212> TYPE: DNA
<213> ORGANISM: Artificial
<220> FEATURE:
<223> OTHER INFORMATION: Description of Artificial Sequence; Synthetic

<400> SEQUENCE: 27
ttcgggaaac cggagctaat accggataat attttgaacc gcatggttca aaagtgaaag     60
acggtcttgc tgtcacttat agatggatcc gcgctgcatt agcta                    105

<210> SEQ ID NO 28
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: Amino group attached at the 5'end
<220> FEATURE:
<221> NAME/KEY: misc_feature
<222> LOCATION: (42)..(42)
<223> OTHER INFORMATION: Aminolink attached at the 3'end

<400> SEQUENCE: 28
cgtctttcac ttttgaacca tgcggttcaa aatattatcc gg                        42

<210> SEQ ID NO 29
<211> LENGTH: 60
<212> TYPE: DNA
<213> ORGANISM: Artificial
<220> FEATURE:
<223> OTHER INFORMATION: Description of Artificial Sequence; Synthetic

<400> SEQUENCE: 29
catctctgct gcccccattc acaccgttc gcctttccga tctataagtg acagcaagac      60
```

```
<210> SEQ ID NO 30
<211> LENGTH: 63
<212> TYPE: DNA
<213> ORGANISM: Artificial
<220> FEATURE:
<223> OTHER INFORMATION: Description of Artificial Sequence; Synthetic

<400> SEQUENCE: 30
catctctgct ggtcccacat tcacacccgt tcgccataga cgatctataa gtgacagcaa      60
gac                                                                    63

<210> SEQ ID NO 31
<211> LENGTH: 66
<212> TYPE: DNA
<213> ORGANISM: Artificial
<220> FEATURE:
<223> OTHER INFORMATION: Description of Artificial Sequence; Synthetic

<400> SEQUENCE: 31
cattctctgc tggtcccaca ttcaacaccc gttcgccata gacagatcta taagtgacag      60
caagac                                                                 66

<210> SEQ ID NO 32
<211> LENGTH: 64
<212> TYPE: DNA
<213> ORGANISM: Artificial
<220> FEATURE:
<223> OTHER INFORMATION: Description of Artificial Sequence; Synthetic

<400> SEQUENCE: 32
catctctgct ggtcccacat tcaacacccg ttcgccatag acgatctata agtgacagca      60
agac                                                                   64

<210> SEQ ID NO 33
<211> LENGTH: 57
<212> TYPE: DNA
<213> ORGANISM: Artificial
<220> FEATURE:
<223> OTHER INFORMATION: Description of Artificial Sequence; Synthetic

<400> SEQUENCE: 33
cactctgctc gccccttcac acccgttcgc cttccgatct ataagtgaca gcaagac         57

<210> SEQ ID NO 34
<211> LENGTH: 69
<212> TYPE: DNA
<213> ORGANISM: Artificial
<220> FEATURE:
<223> OTHER INFORMATION: Description of Artificial Sequence; Synthetic

<400> SEQUENCE: 34
catgtctcgt gtcttcctgc tacagtgaac tcgttctcga cataggtcat ctataagtga      60
cagcaagac                                                              69

<210> SEQ ID NO 35
<211> LENGTH: 72
<212> TYPE: DNA
<213> ORGANISM: Artificial
<220> FEATURE:
<223> OTHER INFORMATION: Description of Artificial Sequence; Synthetic

<400> SEQUENCE: 35
cattctctgc tgtagtccca cattcaacac actcgttctg cacatagaca gatctataag      60
tgacagcaag ac                                                          72
```

<210> SEQ ID NO 36
<211> LENGTH: 75
<212> TYPE: DNA
<213> ORGANISM: Artificial
<220> FEATURE:
<223> OTHER INFORMATION: Description of Artificial Sequence; Synthetic

<400> SEQUENCE: 36
cattctactg ctgtagtccc acattcatac acactcgttc tgcatcatag acagatctat    60
aagtgacagc aagac                                                    75

<210> SEQ ID NO 37
<211> LENGTH: 78
<212> TYPE: DNA
<213> ORGANISM: Artificial
<220> FEATURE:
<223> OTHER INFORMATION: Description of Artificial Sequence; Synthetic

<400> SEQUENCE: 37
cattctactg actgtagtcc cacattcata tcacactcgt tctgacatca tagacagatc    60
tataagtgac agcaagac                                                 78

<210> SEQ ID NO 38
<211> LENGTH: 81
<212> TYPE: DNA
<213> ORGANISM: Artificial
<220> FEATURE:
<223> OTHER INFORMATION: Description of Artificial Sequence; Synthetic

<400> SEQUENCE: 38
cattctactg actgtagttc cacacattca tatcacactc gttctgacat catagacaag    60
atctataagt gacagcaaga c                                             81

<210> SEQ ID NO 39
<211> LENGTH: 39
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 39
catctctgct gcccccattc acaccgttc gcctttccg                           39

<210> SEQ ID NO 40
<211> LENGTH: 39
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 40
ggcagcagag atggggtgtg aatgggcgga aaggcgaac                          39

<210> SEQ ID NO 41
<211> LENGTH: 42
<212> TYPE: DNA
<213> ORGANISM: Artificial

```
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 41
catctctgct ggtcccacat tcacacccgt tcgccataga cg                              42

<210> SEQ ID NO 42
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 42
gaccagcaga gatggggtgt gaatgtggcg tctatggcga ac                              42

<210> SEQ ID NO 43
<211> LENGTH: 45
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 43
cattctctgc tggtcccaca ttcaacaccc gttcgccata gacag                           45

<210> SEQ ID NO 44
<211> LENGTH: 45
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 44
gaccagcaga gaatggggtg ttgaatgtgg ctgtctatgg cgaac                           45

<210> SEQ ID NO 45
<211> LENGTH: 43
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 45
catctctgct ggtcccacat tcaacacccg ttcgccatag acg                             43

<210> SEQ ID NO 46
<211> LENGTH: 43
<212> TYPE: DNA
<213> ORGANISM: Artificial
```

```
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 46
gaccagcaga gatggggtgt tgaatgtggc gtctatggcg aac                    43

<210> SEQ ID NO 47
<211> LENGTH: 36
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 47
cactctgctc gccccttcac acccgttcgc cttccg                            36

<210> SEQ ID NO 48
<211> LENGTH: 36
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 48
gcgagcagag tggggtgtga agggcggaag gcgaac                            36

<210> SEQ ID NO 49
<211> LENGTH: 48
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 49
catgtctcgt gtcttcctgc tacagtgaac tcgttctcga cataggtc               48

<210> SEQ ID NO 50
<211> LENGTH: 48
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 50
gaagacacga gacatggagt tcactgtagc aggacctatg tcgagaac               48

<210> SEQ ID NO 51
<211> LENGTH: 51
<212> TYPE: DNA
<213> ORGANISM: Artificial
```

-continued

```
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 51
cattctctgc tgtagtccca cattcaacac actcgttctg cacatagaca g         51

<210> SEQ ID NO 52
<211> LENGTH: 51
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 52
gactacagca gagaatggag tgtgttgaat gtggctgtct atgtgcagaa c         51

<210> SEQ ID NO 53
<211> LENGTH: 54
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 53
cattctactg ctgtagtccc acattcatac acactcgttc tgcatcatag acag      54

<210> SEQ ID NO 54
<211> LENGTH: 54
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 54
gactacagca gtagaatgga gtgtgtatga atgtggctgt ctatgatgca gaac      54

<210> SEQ ID NO 55
<211> LENGTH: 57
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 55
cattctactg actgtagtcc cacattcata tcacactcgt tctgacatca tagacag   57

<210> SEQ ID NO 56
<211> LENGTH: 57
<212> TYPE: DNA
<213> ORGANISM: Artificial
```

```
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 56
gactacagtc agtagaatgg agtgtgatat gaatgtggct gtctatgatg tcagaac          57

<210> SEQ ID NO 57
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(11)
<223> OTHER INFORMATION: digoxigenin attached at the 5'end

<400> SEQUENCE: 57
cattctactg actgtagttc cacacattca tatcacactc gttctgacat catagacaag       60

<210> SEQ ID NO 58
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 58
gaactacagt cagtagaatg gagtgtgata tgaatgtgtg cttgtctatg atgtcagaac       60
```